(12) United States Patent
Strnad et al.

(10) Patent No.: US 9,668,759 B2
(45) Date of Patent: Jun. 6, 2017

(54) SURGICAL DRILL GUIDE HAVING KEYWAY FOR AXIAL ALIGNMENT OF A FASTENER FOR USE FOR AN ORTHOPEDIC PLATE

(75) Inventors: Lee A. Strnad, Broadview Heights, OH (US); Dustin Ducharme, Stow, OH (US); Andrew J. Leither, Columbus, OH (US); Derek S. Lewis, Copley, OH (US); Amanda Martin, Norton, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1147 days.

(21) Appl. No.: 12/217,632

(22) Filed: Jul. 8, 2008

(65) Prior Publication Data

US 2009/0177208 A1    Jul. 9, 2009

Related U.S. Application Data

(60) Provisional application No. 60/959,097, filed on Jul. 11, 2007.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/17 | (2006.01) | |
| A61B 17/80 | (2006.01) | |

(52) U.S. Cl.
CPC ...... *A61B 17/1728* (2013.01); *A61B 17/1782* (2016.11); *A61B 17/80* (2013.01)

(58) Field of Classification Search
USPC .......................................................... 606/96
See application file for complete search history.

(56) References Cited

U.S. PATENT DOCUMENTS

| | | | |
|---|---|---|---|
| 2,494,229 A | | 1/1950 | Collison |
| 4,870,842 A | * | 10/1989 | Plumer .......................... 70/232 |
| 5,403,322 A | | 4/1995 | Herzenberg et al. |
| 5,415,502 A | | 5/1995 | Dahlin |

(Continued)

FOREIGN PATENT DOCUMENTS

WO    03015650 A1    2/2003

OTHER PUBLICATIONS

International Search Reported dated Apr. 9, 2013.

*Primary Examiner* — David Isabella
*Assistant Examiner* — Christine Nelson
(74) *Attorney, Agent, or Firm* — Duane Morris LLP

(57) ABSTRACT

A surgical drill guide for positioning, aligning, and of holes to be drilled in bone tissue has retaining means that holds the position and alignment of the drill guide body in a releasable manner with respect to a fastener hole in an orthopedic implant. The retaining means is a key guide that mates with a key way or key ways in or around a threaded locking hole of an orthopedic plate for alignment of a pilot hole and method of using the guide. The key guide has 2 to 8 projections that extend in the direction of the axis of the hole, such as hemi cylindrical projections, and the plate has a corresponding female key way that receives the retaining means. The invention also relates to a method of aligning a locking fastener in a plate at a desired angle relative to a bone by using a surgical guide having a key interface with the plate to position and align a pilot hole.

12 Claims, 4 Drawing Sheets

(56) References Cited

U.S. PATENT DOCUMENTS

| | | | |
|---|---|---|---|
| 5,928,244 A | 7/1999 | Tovey et al. | |
| 6,059,789 A | 5/2000 | Dinger et al. | |
| 6,379,364 B1 | 4/2002 | Brace et al. | |
| 7,278,997 B1 | 10/2007 | Mueller et al. | |
| 7,392,674 B1 * | 7/2008 | Grote | 70/232 |
| 7,625,378 B2 | 12/2009 | Foley | |
| 7,763,029 B2 | 7/2010 | Rathbun et al. | |
| 2004/0092947 A1 | 5/2004 | Foley | |
| 2005/0038444 A1 | 2/2005 | Binder, Jr. et al. | |
| 2006/0085077 A1 | 4/2006 | Cook et al. | |
| 2006/0235400 A1 | 10/2006 | Schneider | |
| 2008/0140130 A1 | 6/2008 | Chan et al. | |
| 2009/0003967 A1 * | 1/2009 | Luna | 411/404 |
| 2009/0204157 A1 | 8/2009 | Dell'Oca | |
| 2010/0130983 A1 | 5/2010 | Thornhill et al. | |

* cited by examiner

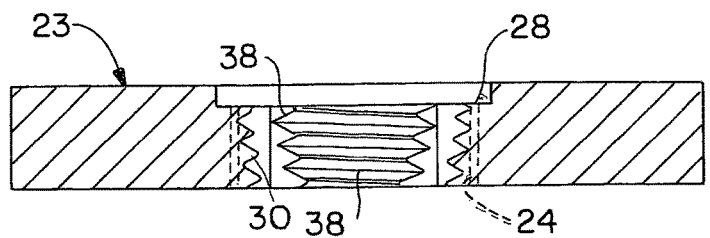
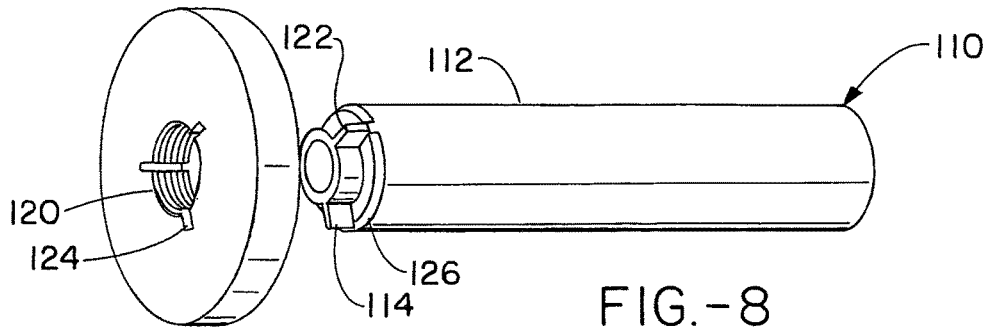
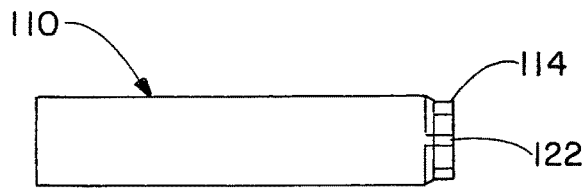
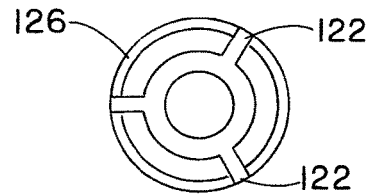
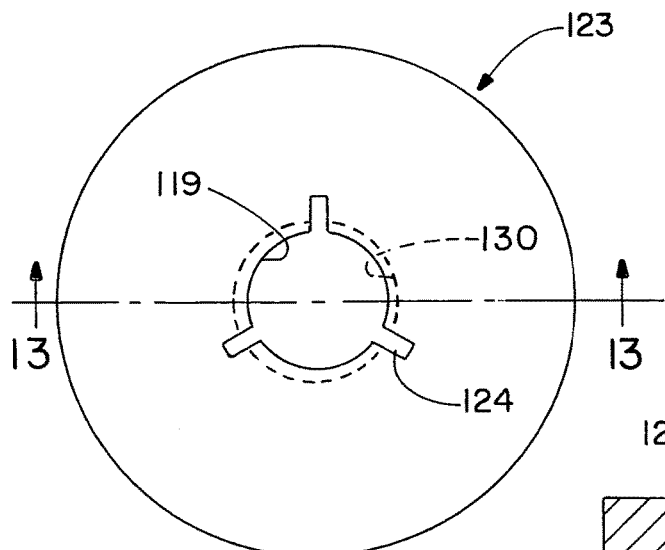
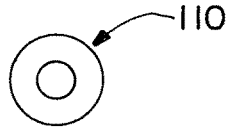
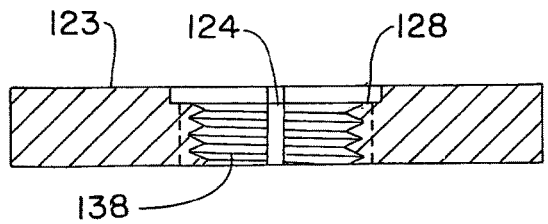

SURGICAL DRILL GUIDE HAVING KEYWAY FOR AXIAL ALIGNMENT OF A FASTENER FOR USE FOR AN ORTHOPEDIC PLATE

CROSS REFERENCE

This application claims the benefit of priority under 35 U.S.C. §119 of U.S. Provisional Application Ser. No. 60/959,097 filed on Jul. 11, 2007.

FIELD OF THE INVENTION

The present invention relates generally to surgical drill guides. More specifically, the present invention relates to surgical drill guides used with corresponding orthopedic implants for positioning and orienting holes to be drilled in bone tissue for receiving a fastener which has a locking relationship to the implant.

BACKGROUND OF THE INVENTION

As the field of orthopedics has advanced, increasing types of constructs have been developed for implantation into human and other animal bodies. There is heightened sophistication in the interplay between the implant, the bone, or bones, the surrounding soft tissue, and the fastener. For example, as the field has developed an understanding has also developed that an implant, such as a plate, can be used to support bone fragments in close, or even compressed association in order to promote the fusion of the fragments, or segments. This has lead to plates, which have a structure that is increasingly designed to function in the healing process, rather than merely acting as a scaffold. For example, an orthopedic surgeon can use an orthopedic implant to reduce a fracture or to rebuild a shattered bone, as well to hold segments of a joint in compression to allow for fusion. Thus, the implant is designed with the understanding that the biological environment is not ever exactly static, and the forces that are applied by the implant to the bone, and by the bone and soft tissue back to the implant will influence the healing or even the restructuring of a bone or bones. Moreover, these plates are increasingly structured to have an anatomical contouring rather than a flat planar shape.

An essential aspect of the proper functioning of the construct is the fastening means that forms the attachment between the implant and the bone. These fastening means can include various types of screws, threaded and non-threaded pegs, k-wires, hooks and other anchoring means. The implants typically include plates, rods, spacers, and cages and implants can include multiple fasteners. Further, the fasteners have various types of interfaces with the implant, including a multiaxial relationship, or a locking relationship or a locking variable axial relationship. In the instance in which the fastener has a ball and socket interface with the implant, the angle at which the fastener is held in the bone is less critical since the implant can receive the fastener at a variety of angles. However, in some instances, it is desirable that the plate be held to the plate at a defined angle. In the prior art, plate surfaces might be planar, and the fastener simply resided in the bone more or less perpendicular to the plate. However, much more sophisticated plate design may dictate fastener holes in the plate that are at a desired angle in a non-planar plate. In this instance, the plate surface is no longer a satisfactory reference for determining the angle to drill in the bone for receiving the fastener.

Constructs are often designed so that the fasteners will reside in the bone and locked relative to the plate at a desired angle so that the construct achieves the optimal stability, the optimal pull-out values for the fasteners, and or the optimal fixation for typical fragments. There are present designs in distal radius plates, as an example, typically where pegs are located and angled to capture various types of fragments that result from the most common breaks. These plates might have a head design with 4 or 7 holes at designated angles so that a surgeon has the option of choosing one, two, all, or some number in between, in order to best set a broken radial fracture.

Often the surgical procedure includes a step of drilling holes in the bone or bones in order to accommodate fastening devices such as screws or pegs used to anchor implants within a patient's body. For instance, screws have been used to anchor plate systems to the long bones of patients for stabilizing a variety of fractures or correcting disorders.

One commonly used technique for inserting a fastening screw into the bone includes the preparation of a pilot hole through the cortical surface of the bone and into the cancellous portion before inserting the screw therein. Typically, the selection of the insertion point is made based on the desired placement of the plate on the bone in relation to the break. Once the insertion point has been selected, a drill guide may be used separately or in conjunction with the plate to guide the drill bit along a desired axis, and/or to set the depth to which the drill bit penetrates the bone. These guides typically have a distal end, which may screw into an internal thread if the plate hole is threaded. Alternatively, the guides may include a tapered end, which can be jammed into the hole. While the former style of guide has the advantage of setting the angle for the screw relative to the plate, it can be cumbersome, time consuming and often difficult to screw the drill guide into these holes. While the taper fit has the advantage of a relatively easy interface, it does not guarantee the angle of the axis of the screw, in the bone or relative to the plate. One prior art guide include an overlay that is fixed to a distal radius plate to fix the angles of multiple holes for various screws or pegs used to fix the head to the distal portion of the radius bone.

The present invention relates to a surgical drill guide having a drill guide body which receives and guides a drill bit and which has a distal end for placement through a mating opening in a bone implant so that the distal end is substantially adjacent an exterior surface of a bone which is intended to receive a bone fastener. The implant is specifically a plate. The drill guide can be used with locking or non-locking fasteners, but is advantageously used with locking fasteners in which the angle of the fastener relative to the axis of the fastener hole is critical to proper functioning of the construct. Thus, the invention relates most specifically to a drill guide system comprising a drill guide used in conjunction with a plate having a threaded hole which receives the threaded head of a bone fastener. The distal end of the drill guide includes an interface which mates with the plate so as to position the drill guide for placement and axial alignment of a hole in the bone that receives a fastener for the implant. The body of the drill guide is held in place relative to the implant so as to define the angle as well as the location of the fastener hole in the bone.

The drill guide of the present invention that has the ease and simplicity of use of a single hole drill guide. This allows the surgeon the best visual access to the bone, but as it has an interface that forms a removable key fit with the plate so that the guide that can be easily inserted and locked from rotation, as well as into a specified angle relative to the screw hole. By "key fit" it is meant that there is a relationship which is a sliding relationship in the longitudinal direction and in a radial direction about that longitudinal axis, there is a radial locking relationship such is formed between a channel having a complex or non circular cross-section. After the pilot hole has been drilled, the drill guide is easily and quickly removed from engagement with the key hole in the plate and moved to a further hole in the plate.

The key fit preferably includes the mating interface between the longitudinal surface of the drill guide tip and recesses (which interrupt the thread) in or around the fastener hole in the plate, which can be a keyway and key that is formed by projections that are respectively hemi-cylindrical, or more ridge-like contiguous (meaning proximal to or adjacent in space) radial (meaning extending radially when viewed in a cross section) projections along the long axis of the drill guide tip that mate with corresponding female shaped recesses in or around the fastener hole. There can be two or more projections, with two to six, and preferably three or four, being ideal. Fewer projection decrease the possibility of stripping the projections and increase the security of the locking, while more projections make it easier to find the proper orientation of the drill guide tip in the recess. Also, the drill guide may include a flat shoulder that seats on a flat internal surface of the fastener recess. Thus, the fastener hole may include a counterbore defining a rim that captures a shoulder on the drill guide tip. The drill guide may also include a means to determine the drill depth, such as a marked fenestration along the shaft of the drill guide body.

SUMMARY OF THE INVENTION

The present invention is directed to a surgical drill guide. The drill guide may include a drill guide body having a distal end for placement through a fastening hole or holes in an implant, such as a plate and substantially adjacent a bone. The drill guide body further includes a proximal end with an opening into a through bore for receiving and guiding a drill bit. The distal end of the drill guide includes an interface with the plate that releasably retains the position of the drill guide body with respect to the fastening hole. The interface preferably comprises a key having multiple lobes or projections (i.e., from 2 to 8 or preferably 6, and more preferably 3 or 4), which mates with corresponding females recesses that form key ways in or about the fastener recess to hold the drill guide in position in the recess. Further, the interface includes means to hold the axial positioning of the drill guide relative to the plate in order to fix the angle of the fastener relative to the plate. These lobes or projections may reside within the threads or any other location within the plate.

BRIEF DESCRIPTION OF THE DRAWINGS

The invention will be better understood and other features and advantages will become apparent by reading the detailed description of the invention, taken together with the drawings, wherein:

FIG. 7 is a cross section of the recess of FIG. 6 taken at line 7-7;

FIG. 8 is a perspective view of an alternative embodiment of the drill guide with a mating threaded locking hole in accordance with the present invention;

FIG. 9 is a side view of the drill guide of FIG. 8;

FIG. 10 is an end view showing the alignment tip of the drill guide of FIG. 8;

FIG. 11 is a view from the other end of the drill guide of FIG. 8;

FIG. 12 is a top view of a detail from a plate showing the fastener recess which receives the detent tip of the drill guide of FIG. 8;

FIG. 13 is a cross section of the recess in a plate taken at line 13-13 of FIG. 12;

DETAILED DESCRIPTION OF THE PREFERRED EMBODIMENTS

Figure 1:
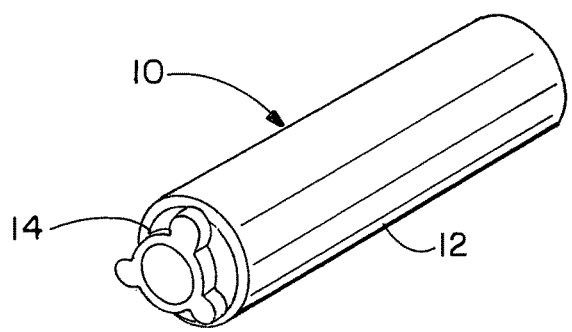
FIG. 1 is a perspective view of the drill guide in accordance with the present invention.
Figure 2:
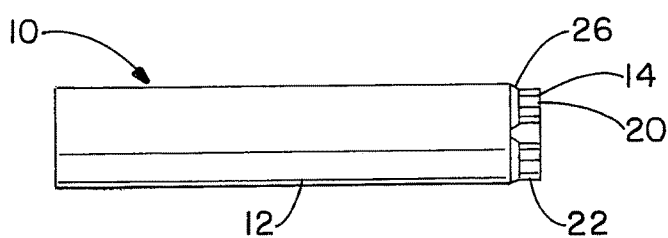
FIG. 2 is a side view of the drill guide of FIG. 1.
Figure 3:
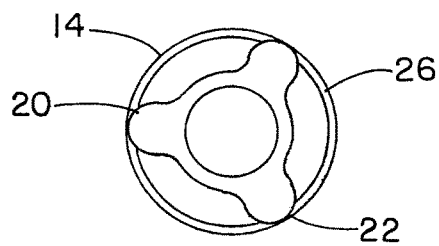
FIG. 3 is an end view showing the alignment tip of the drill guide of FIG. 1.
Figure 4:
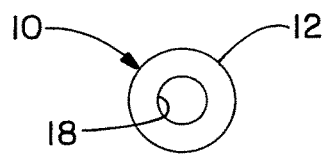
FIG. 4 is a view from the other end of the drill guide of FIG. 1.
Figure 5:
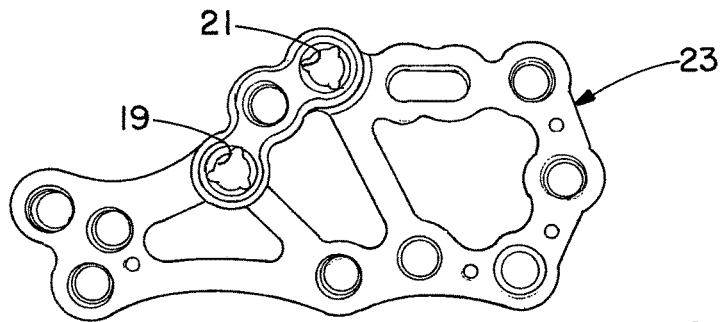
FIG. 5 is a top view of a plate having a threaded recess for a locking screw and further being configured to receive the alignment tip of the drill guide of FIG. 1.
Figure 6:
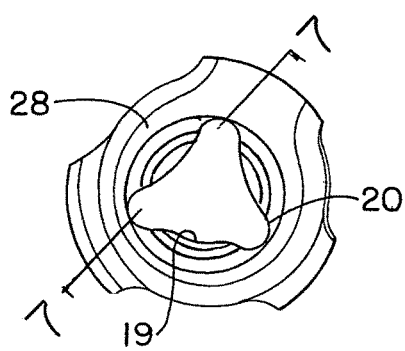
FIG. 6 is a detail of a threaded recess for a locking screw from FIG. 5.

Referring to FIGS. 1 and 2, an illustrative embodiment of a surgical drill guide according to the present invention is shown. Drill guide 10 includes a drill guide body 12 with a proximal end and a distal end which includes a drill guide tip 14. The drill guide body 12 has an opening 18 that extends through the body 12 so as to form a substantially tubular shaft which defines a cannula for receiving a drill bit. The shaft terminates in the drill guide tip 14 which includes an aligning mechanism that defines the angle and position of the cannula so as to guide a drill bit for a desired angle and position for a pilot hole for a fastener.

The aligning mechanism 20 comprises a mating interface with the implant (which is preferably a plate) with which the drill guide is used. This preferably includes a mating interface between the longitudinal surfaces of the drill guide tip and recesses 21 in the fastener hole 19 of the plate 23, which can comprise a key having a compound configuration in cross section and key way having a mating female configuration where the key is comprised of a center portion with hemi-cylindrical, or more ridge-like radial projections 22 which extend along the drill guide tip in the direction of the long axis of the drill guide tip and that mate with corresponding female shaped recesses 24 along the long axis and "contiguous with", meaning adjacent to the periphery, of the screw hole. There can be two or more projections, with two to six, and preferably three or four, being ideal. Fewer projections are less disruptive to the internal locking threads of the fastener hole, while more projections make it easier to find the proper orientation of the drill guide tip in the recess. Also, the drill guide may include a shoulder 26 that seats on an internal surface 28 such as is formed by a counterbore at the opening to the fastener recess. The fastener recess also includes internal threads 30 that receive external threads on the head of a locking screw. The alignment recesses can also be external to or longitudinally superior to the threads.

An alternate embodiment of the drill guide 110 of the present invention is shown in FIG. 8. This guide includes a drill guide tip 114 with a similar aligning mechanism 120 in plate 123. In this embodiment, the projections 122 are planar (i.e. forming a portion of a rectangle in cross-section) and the female aligning recesses 124 are also planar. The tip includes the shoulder 126 which seats on a rim 128 formed in the fastening recess 119. The recess 119 also includes internal threads 130 that receive the external threads 138 of a locking screw or peg.

Figure 14:
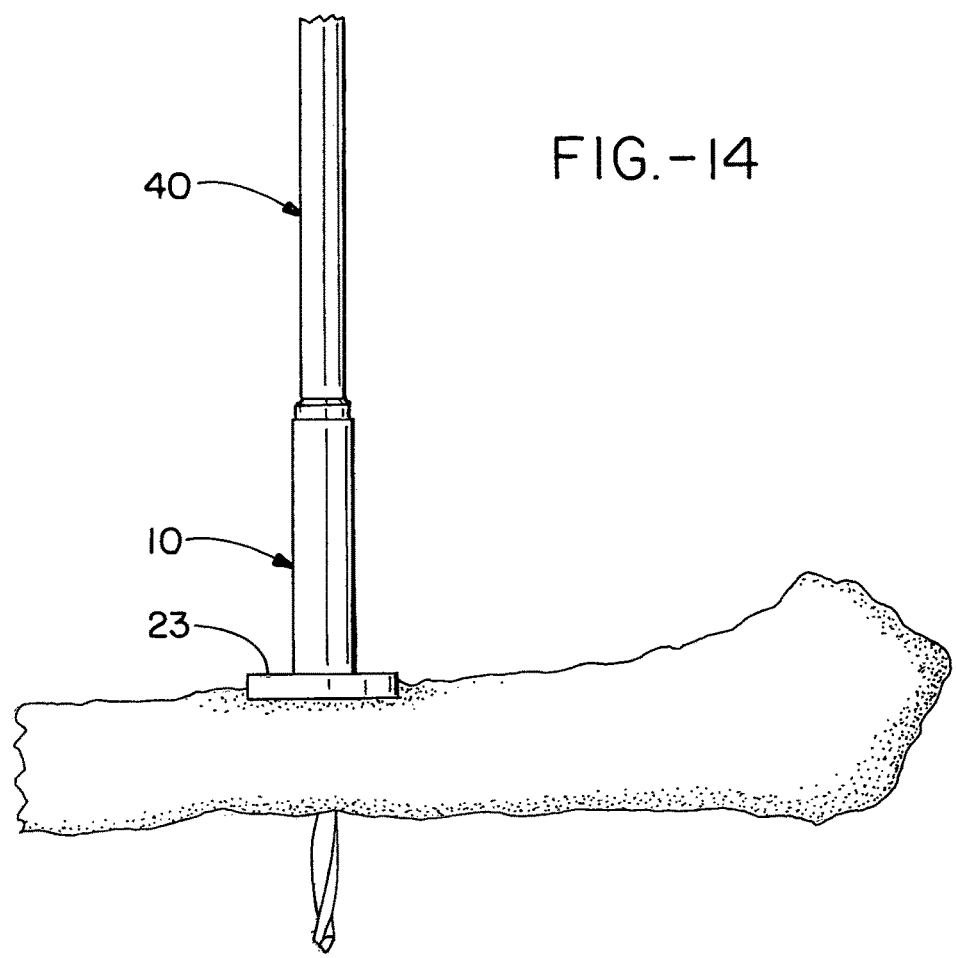
FIG. 14 is a side view of the drill guide with a drill in use to drill a hole through a recess in a plate into a bone.

FIG. 14 shows a drill 40 engaged in a drill guide of the present invention boring a hole in a bone.

Figure 15:
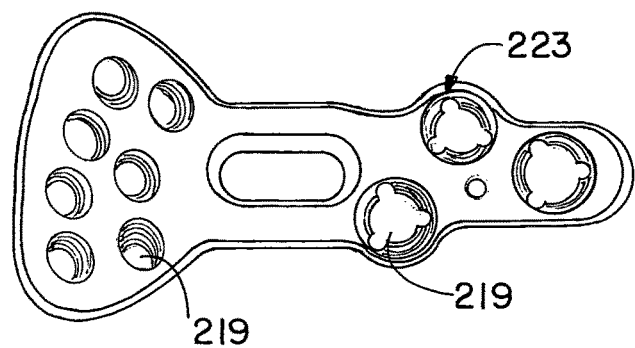
FIG. 15 is a top view of a distal radius plate illustrating the use of the present invention in yet another implant.
Figure 16:
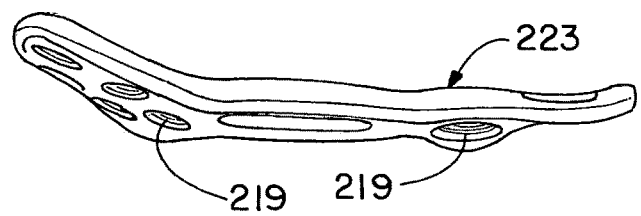
FIG. 16 is a side view of the distal radius plate of FIG. 15.
Figure 17:
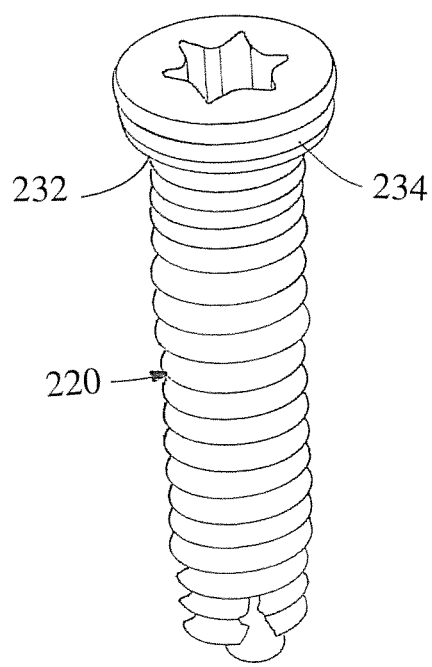
FIG. 17 is a top side view of a threaded locking screw.

FIGS. 15 and 16 illustrate a distal radius plate 223 having threaded through holes 219 for locking fasteners 220, shown in FIG. 17 and having head 232 with external threads 234 and which are designed to receive the fasteners at specific angles in order to facilitate the optimal restructuring of typical fractures during surgery.

The invention also relates to a method of forming a bone construct for a bone that comprises a plate having one or more through holes for a fastener, and in particular where one of more of the holes include an internal thread that mates with a threaded portion on the fastener, comprising the step of placing the plate on the bone and using a drill guide having a distal end having at least one longitudinally extending projection that mates with a corresponding recess in the plate to hold the drill guide at a desired angle relative to the bone, and using the drill guide to guide the angle of a hole in the bone for a fastener which extends through the plate into the hole in the bone and which is locked at a desired angle relative to the plate by the mating of the internal thread in the hole in the plate with the threaded portion of the fastener.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments, which come within the spirit and scope of the present invention.

What is claimed is:

1. A drill guide system for positioning and aligning a pilot hole drilled by a drill in a bone comprising:
    a drill guide, a locking fastener having a head including external threads, and a plate having at least one fastener recess including a circular recess portion which defines a longitudinal axis for a locking fastener and has internal threads that are capable of receiving the external threads on the head of the locking fastener,
    the drill guide having a drill guide body with a first end and a second end and a cannula therethrough, the second end of the drill guide body having a drill guide tip including a cylindrical central aligning tip which has at least two contiguous radial projections that extend along the central aligning tip in the direction of the longitudinal axis, and the fastener recess including at least two respective female aligning recesses which are contiguous with the circular recess portion and that reside within the internal threaded recess whereby the internal threads are interrupted by the female aligning recesses, and which form a mating interface between the drill guide tip and the fastener recess of the plate that defines a key fit in the fastener recess with the at least two radial projections of the drill guide tip so as to define an angle of the cannula of the drill guide and an angle of the pilot hole so as to define the angle of the locking fastener in use so that the locking fastener is locked at a specified angle relative to the plate by the mating of the internal threads in the at least one fastener recess in the plate with the external threads on the head of the locking fastener.

2. The drill guide system as set forth in claim 1 wherein the drill guide tip has from 3 to 8 projections.

3. The drill guide system as set forth in claim 2 wherein the projections are hemi-cylindrical or planar flanges.

4. The drill guide system as set forth in claim 3 wherein there are 3 or 4 projections.

5. The drill guide system as set forth in claim 1 wherein the drill guide tip has a flat shoulder and the fastener recess further includes a counterbore that defines a rim having a flat internal surface so that the shoulder seats on the flat internal surface such that the rim captures the flat shoulder in use.

6. A drill guide system for positioning and aligning a hole drilled by a drill in a bone comprising:
    a drill guide and a plate having a top surface and a bottom surface and at least one fastener recess extending between the top surface and the bottom surface and which defines a longitudinal axis for a fastener and has a cylindrical portion having internal threads,
    the drill guide having a drill guide body and a first end and a second end with a cannula therethrough, the second end of the drill guide body including an aligning tip which has at least one contiguous key comprising a radial projection that extends in the direction of the longitudinal axis, and the fastener recess including at least one key way in the fastener recess comprising a female aligning recess extending between the top surface and the bottom surface and which is contiguous to the cylindrical portion having internal threads whereby the internal threads are interrupted by the female aligning recess, and which forms a mating interface so as to define a key fit with the key in the fastener recess in the area between the top surface and the bottom surface so as to define an angle of the cannula of the drill guide.

7. The drill guide system as set forth in claim 6 wherein the aligning tip has from 2 to 8 projections.

8. The drill guide system as set forth in claim 7 wherein the projections are hemi-cylindrical or planar flanges.

9. The drill guide system as set forth in claim 8 wherein there are 3 or 4 projections.

10. The drill guide system as set forth in claim 6 wherein the drill guide tip has a flat shoulder and the fastener recess further includes a counterbore that defines a rim having a flat internal surface so that the shoulder seats on the flat internal surface such that the rim captures the flat shoulder in use.

11. A drill guide system for positioning and aligning a pilot hole drilled by a drill in a bone comprising:
    a drill guide having a longitudinal axis and a drill guide body with a first end and a second end and a cannula therethrough, the second end of the drill guide body having a drill guide tip including a cylindrical central aligning tip and at least two longitudinal ridges that extend along the central aligning tip in a direction of the longitudinal axis, the longitudinal ridges beginning at a cylindrical outer surface of the cylindrical central aligning tip and extending radially outward from the cylindrical outer surface;
    a locking fastener having a head including external threads, and
    a plate having at least one fastener recess including a circular recess portion which defines a longitudinal axis for the locking fastener and has internal threads that are capable of receiving the external threads on the head of the locking fastener, wherein the fastener recess includes at least two respective female aligning recesses which are contiguous with the circular recess portion and shaped to slidably receive the respective longitudinal ridges, whereby the internal threads of the circular recess portion are interrupted by the female aligning recesses, so the drill guide tip is slidable in the direction of the longitudinal axis into the fastener recess, for locking the drill guide from rotation as long as the longitudinal ridges of the drill guide tip are in the respective female aligning recesses of the fastener recess.

12. The system of claim 11, wherein:

the drill guide tip has a flat shoulder configured to seat on a flat internal surface of the fastener recess; and the fastener recess includes a counterbore having a rim that receives the shoulder of the drill guide tip.

\* \* \* \* \*